United States Patent
Yang et al.

(10) Patent No.: US 11,862,296 B2
(45) Date of Patent: Jan. 2, 2024

(54) METHOD FOR DESIGNING MULTI-OBJECTIVE PRIMER PAIR

(71) Applicant: National Kaohsiung University of Science and Technology, Kaohsiung (TW)

(72) Inventors: Cheng-Hong Yang, Kaohsiung (TW); Li-Yeh Chuang, Kaohsiung (TW); Yu-Da Lin, Kaohsiung (TW)

(73) Assignee: NATIONAL KAOHSIUNG UNIVERSITY OF SCIENCE AND TECHNOLOGY, Kaohsiung (TW)

( * ) Notice: Subject to any disclaimer, the term of this patent is extended or adjusted under 35 U.S.C. 154(b) by 396 days.

(21) Appl. No.: 17/202,953

(22) Filed: Mar. 16, 2021

(65) Prior Publication Data
US 2022/0208304 A1 Jun. 30, 2022

(30) Foreign Application Priority Data
Dec. 25, 2020 (TW) .................. 109146308

(51) Int. Cl.
*G16B 25/20* (2019.01)
(52) U.S. Cl.
CPC .................. *G16B 25/20* (2019.02)
(58) Field of Classification Search
None
See application file for complete search history.

(56) References Cited

PUBLICATIONS

Raharjo, CD. Prototype of application multi-objective genetic algorithm using multi-threading strategy with thinking design approach method for optimization design DNA primer and DNA probe. 1st International Conference on Bioinformatics, Biotechnology, and Biomedical Engineering, pp. 1-6. (Year: 2018).*
Michael C. Riley, Wayne Aubrey, Michael Young and Amanda Clare, "PD5: A General Purpose Library for Primer Design Software", PLoS ONE, Nov. 21, 2013, vol. 8, Issue 11.
Francesco Sambo, Francesca Finotello, Enrico Lavezzo, Giacomo Baruzzo, Giulia Masi, Elektra Peta, Marco Falda, Stefano Toppo, Luisa Barzon and Barbara Di Camillo, "Optimizing PCR primers targeting the bacterial 16S ribosomal RNA gene", BMC Bioinformatics, Sep. 29, 2018, vol. 19.

* cited by examiner

*Primary Examiner* — G. Steven Vanni
*Assistant Examiner* — Robert James Kallal
(74) *Attorney, Agent, or Firm* — WPAT, PC

(57) ABSTRACT

A method for designing a multi-objective primer pair is disclosed. The method includes inputting a DNA template fragment, a length of a forward primer, a length of a reverse primer, at least two objectives and optimal values for each of the at least two objectives to a computer system; generating, by the computer system, a plurality of primer pairs according to the DNA template fragment, the length of the forward primer and the length of the reverse primer; and calculating, by the computer system, numerical values of the at least two objectives of each of the plurality of primer pairs and inputting the numerical values of the at least two objectives of each of the plurality of primer pairs to a Pareto Chart tool to obtain at least one primer pair, and taking the primer pair as an optimal solution of the DNA template fragment.

8 Claims, 1 Drawing Sheet

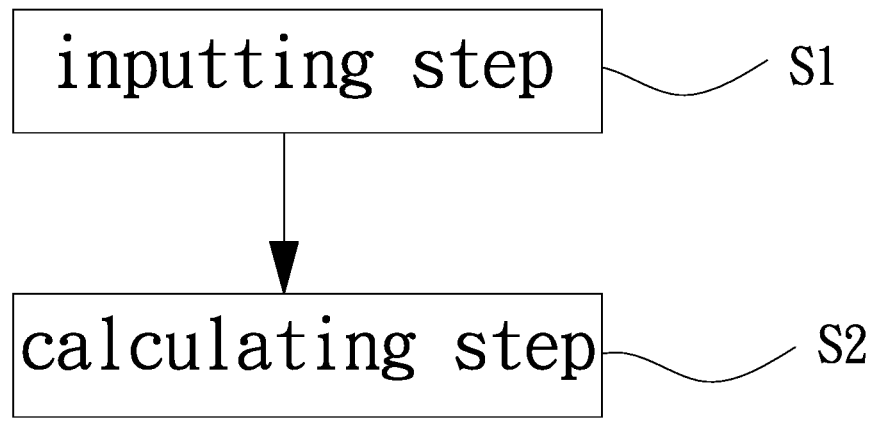

US 11,862,296 B2

METHOD FOR DESIGNING MULTI-OBJECTIVE PRIMER PAIR

CROSS REFERENCE TO RELATED APPLICATION

The application claims the benefit of Taiwan application serial No. 109146308, filed on Dec. 25, 2020, and the entire contents of which are incorporated herein by reference.

BACKGROUND OF THE INVENTION

1. Field of the Invention

The present invention generally relates to a method for designing a multi-objective primer pair and, more particularly, to a design method using a plurality of objectives as the restricted condition for designing the primer pair.

2. Description of the Related Art

Polymerase chain reaction (PCR), a chain replication technique with specificity, can replicate a plenty of gene sequences. A primer is single stranded oligonucleotide that is taken as a starting point for replication of PCR. As different primers will influence products of PCR, the restricted condition for the primers must be considered when designing the primers.

Conventional primer pair design methods use objectives such as a melting temperature, a GC clamp, a GC proportion (GC %) and a formation of dimer (self-dimer or cross-dimer) or formation of a hairpin as the restricted condition and adding up and convert all objectives into a single-objective for evaluation. However, the conventional primer pair design methods cannot set an optimal value for each objective because when a primer pair is designed according to the added-up single-objective, even if a numerical value is optimal corresponding to the objective, a numerical result of the primer pair with regard to other objectives may not meet the requirements thereof. For example, a difference between the calculated numerical value and the optimal value may be very large. Thus, the conventional primer pair design methods may have problems of poor primer design efficiency and high time and consumable costs of a PCR experiment.

In light of this, it is necessary to provide an improved primer pair design method to solve the problems mentioned above.

SUMMARY OF THE INVENTION

It is therefore an aim of the present invention to provide a method for designing a multi-objective primer pair, which can simultaneously use a plurality of objectives as the restricted condition for designing the primer pair.

It is another aim of the present invention to provide the method for designing the multi-objective primer pair, which can set an optimal value for each of the plurality of objectives and making the numerical value of each objective of the designed primer pair meet the corresponding optimal value.

The "first objective" herein calculates a difference between the melting temperature of a forward primer and a set optimal melting temperature of the forward primer and takes an absolute value thereof. The melting temperature of the forward primer is a temperature at which a double-stranded DNA template fragment of the forward primer is opened by 50% to form the single-stranded forward primer.

The "second objective" herein calculates a difference between the melting temperature of a reverse primer and a set optimal melting temperature of the reverse primer and takes an absolute value thereof. The melting temperature of the reverse primer is a temperature at which a double-stranded DNA template fragment of the reverse primer is opened by 50% to form the single-stranded reverse primer.

The "third objective" calculates a temperature difference between the melting temperatures of the forward primer and the reverse primer and takes an absolute value to obtain a first difference value, calculates a temperature difference between the optimal melting temperature of the forward primer and the optimal melting temperature of the reverse primer and takes an absolute value to obtain a second difference value. If the first difference value is not greater than the second difference value, the third objective is equal to 0, and if the first difference value is greater than the second difference value, the third objective is equal to a difference between the first difference value and the second difference value.

The "fourth objective" herein confirms whether nucleotide types in 3' ends of both the forward primer and the reverse primer are 'G' or 'C', and if yes, a GC clamp of the primer pair formed by the forward primer and the reverse primer is equal to 0; confirms whether nucleotide types in the 3' ends of either the forward primer or the reverse primer are 'G' or 'C', and if yes, the CG clamp is equal to 1; confirms whether nucleotide types in the 3' ends of the forward primer and the reverse primer are neither 'G' nor 'C', and if yes, the GC clamp is equal to 2; calculates a length difference between the forward primer and the reverse primer and takes an absolute value thereof to obtain a first length; sets an optimal length of the forward primer and an optimal length of the reverse primer and calculates a difference between the optimal length of the forward primer and the optimal length of the reverse primer and takes an absolute value thereof to obtain a second length. If the first length is not greater than the second length, a length difference is equal to 0, and if the first length is greater than the second length, the length difference is equal to a difference between the first length and the second length, and the fourth objective is equal to a sum of the GC clamp and the length difference.

The "fifth objective" herein calculates a difference between a proportion of 'G' and 'C' type nucleotides in the forward primer and a set optimal GC proportion of the forward primer and takes an absolute value thereof.

The "sixth objective" herein calculates a proportion of 'G' and 'C' type nucleotides in the reverse primer and a set optimal GC proportion of the reverse primer and takes an absolute value thereof.

The "seventh objective" herein calculates the quantity of bindings generated by the nucleotides of two forward primers of a plurality of forward primers and a plurality of reverse primers provided simultaneously when a polymerase chain reaction is carried out to obtain a first quantity. If the first quantity is not greater than an optimal forward primer self-binding quantity, a forward primer self-binding quantity is equal to 0; and if the first quantity is greater than the optimal forward primer self-binding quantity, the forward primer self-binding quantity is equal to a difference between the first quantity and the optimal forward primer self-binding quantity. Calculate the quantity of bindings generated by the nucleotides of two reverse primers to obtain a second quantity. If the second quantity is greater than an optimal reverse primer self-binding quantity, the reverse primer self-binding quantity is equal to a difference between the second quantity and the optimal reverse primer self-binding quantity. Calculate the quantity of bindings generated by the nucleotides of one of the plurality of forward primers and one of the plurality of reverse primers to obtain a third quantity. If the third quantity is not greater than an optimal cross-binding quantity, a primer cross-binding quantity is equal to 0; and if the third quantity is greater than the optimal cross-binding quantity, the primer cross-binding quantity is equal to a difference between the third quantity and the optimal cross-binding quantity. The seventh objective is equal to a sum of the forward primer self-binding quantity, the reverse primer self-binding quantity and the primer cross-binding quantity.

The "eighth objective" herein calculates the quantity of self-annealings generated by the nucleotides of one forward primer of a plurality of forward primers and a plurality of reverse primers provided simultaneously when a polymerase chain reaction is carried out to obtain a fourth quantity. If the fourth quantity is not greater than an optimal forward primer self-annealing quantity, a forward primer self-annealing quantity is equal to 0; if the fourth quantity is greater than the optimal forward primer self-annealing quantity, the forward primer self-annealing quantity is equal to a difference between the fourth quantity and the optimal forward primer self-annealing quantity. Calculate the quantity of self-annealings generated by the nucleotides of one reverse primer to obtain a fifth quantity. If the fifth quantity is not greater than an optimal reverse primer self-annealing quantity, a reverse primer self-annealing quantity is equal to 0; and if the fifth quantity is greater than the optimal reverse primer self-annealing quantity, the reverse primer self-annealing quantity is equal to a difference between the fifth quantity and the optimal reverse primer self-annealing quantity. Calculate a specificity of the primer pair formed by the forward primer and the reverse primer and multiplying by a time to obtain a specificity value; and the eighth objective is equal to a sum of the forward primer self-annealing quantity, the reverse primer self-annealing quantity and the specificity value.

As used herein, the term "a", "an", or "one" for describing the number of the elements and members of the present invention is used for convenience, provides the general meaning of the scope of the present invention, and should be interpreted to include one or at least one. Furthermore, unless explicitly indicated otherwise, the concept of a single component also includes the case of plural components.

A method for designing a multi-objective primer pair includes inputting a DNA template fragment, a length of a forward primer, a length of a reverse primer, at least two objectives and optimal values for each of the at least two objectives to a computer system; generating, by the computer system, a plurality of primer pairs according to the DNA template fragment, the length of the forward primer and the length of the reverse primer; and calculating, by the computer system, numerical values of the at least two objectives of each of the plurality of primer pairs and inputting the numerical values of the at least two objectives of each of the plurality of primer pairs to a Pareto Chart tool to obtain at least one primer pair, and taking the primer pair as an optimal solution of the DNA template fragment.

Accordingly, the method for designing the multi-objective primer pair according to the present invention may permit a user to set the optimal value for the selected objective and take the prime pair that a difference between the numerical value of the objective and the corresponding optimal value is small as an optimal solution. Thus, the method for designing the multi-objective primer pair according to the present invention can avoid a large difference between the numerical value of the selected objective and the optimal value, improving the primer pair design efficiency and lowering the time and consumable costs of the PCR experiment.

In an example, the at least one primer pair is a prime pair that a difference between the numerical value of the objective obtained through the Pareto Chart tool and the corresponding optimal value is small. Thus, the method is able to achieve the effect that the numerical values of the objectives calculated by the plurality of primer pairs do not govern each other when there is a plurality of primer pairs.

In an example, the at least two objectives include a first objective calculating a difference between a melting temperature of the forward primer and a set optimal melting temperature of the forward primer and taking an absolute value thereof.

In an example, the at least two objectives include a second objective calculating a difference between a melting temperature of the reverse primer and a set optimal melting temperature of the reverse primer and taking an absolute value thereof.

In an example, the at least two objectives include a third objective calculating a difference between a melting temperature of the forward primer and a melting temperature of the reverse primer and taking an absolute value thereof to obtain a first difference value, calculating a difference between an optimal melting temperature of the forward primer and an optimal melting temperature of the optimal reverse primer and taking an absolute value thereof to obtain a second difference value, wherein if the first difference value is not greater than the second difference value, the third objective is equal to 0, and if the first difference value is greater than the second difference value, the third objective is equal to a difference between the first difference value and the second difference value.

In an example, the at least two objectives include a fourth objective confirming whether nucleotide types in 3' ends of both the forward primer and the reverse primer are 'G' or 'C', and if yes, a GC clamp of the primer pair formed by the forward primer and the reverse primer is equal to 0; confirming whether nucleotide types in the 3' ends of either the forward primer or the reverse primer are 'G' or 'C', and if yes, the CG clamp is equal to 1; confirming whether nucleotide types in the 3' ends of the forward primer and the reverse primer are neither 'G' nor 'C', and if yes, the GC clamp is equal to 2; calculating a length difference between the forward primer and the reverse primer and taking an absolute value thereof to obtain a first length; setting an optimal length of the forward primer and an optimal length of the reverse primer and calculating a difference between the optimal length of the forward primer and the optimal length of the reverse primer and taking an absolute value thereof to obtain a second length. If the first length is not greater than the second length, a length difference is equal to 0, and if the first length is greater than the second length, the length difference is equal to a difference between the first length and the second length, and the fourth objective is equal to a sum of the GC clamp and the length difference.

In an example, the at least two objectives include a fifth objective calculating a difference between a proportion of 'G' and 'C' type nucleotides in the forward primer and a set optimal GC proportion of the forward primer and taking an absolute value thereof.

In an example, the at least two objectives include a sixth objective calculating a proportion of 'G' and 'C' type nucleotides contained in the reverse primer and a set optimal GC proportion of the reverse primer and taking an absolute value thereof.

In an example, the at least two objectives include a seventh objective calculating the quantity of bindings generated by the nucleotides of two forward primers of a plurality of forward primers and a plurality of reverse primers provided simultaneously when a polymerase chain reaction is carried out to obtain a first quantity. If the first quantity is not greater than an optimal forward primer self-binding quantity, a forward primer self-binding quantity is equal to 0; and if the first quantity is greater than the optimal forward primer self-binding quantity, the forward primer self-binding quantity is equal to a difference between the first quantity and the optimal forward primer self-binding quantity. Calculate the quantity of bindings generated by the nucleotides of two reverse primers to obtain a second quantity. If the second quantity is greater than an optimal reverse primer self-binding quantity, the reverse primer self-binding quantity is equal to a difference between the second quantity and the optimal reverse primer self-binding quantity. Calculate the quantity of bindings generated by the nucleotides of one of the plurality of forward primers and one of the plurality of reverse primers to obtain a third quantity. If the third quantity is not greater than an optimal cross-binding quantity, a primer cross-binding quantity is equal to 0; and if the third quantity is greater than the optimal cross-binding quantity, the primer cross-binding quantity is equal to a difference between the third quantity and the optimal cross-binding quantity. The seventh objective is equal to a sum of the forward primer self-binding quantity, the reverse primer self-binding quantity and the primer cross-binding quantity.

The at least two objectives include an eighth objective calculating the quantity of self-annealings generated by the nucleotides of one forward primer of a plurality of forward primers and a plurality of reverse primers provided simultaneously when a polymerase chain reaction is carried out to obtain a fourth quantity. If the fourth quantity is not greater than an optimal forward primer self-annealing quantity, a forward primer self-annealing quantity is equal to 0; if the fourth quantity is greater than the optimal forward primer self-annealing quantity, the forward primer self-annealing quantity is equal to a difference between the fourth quantity and the optimal forward primer self-annealing quantity. Calculate the quantity of self-annealings generated by the nucleotides of one reverse primer to obtain a fifth quantity. If the fifth quantity is not greater than an optimal reverse primer self-annealing quantity, a reverse primer self-annealing quantity is equal to 0; and if the fifth quantity is greater than the optimal reverse primer self-annealing quantity, the reverse primer self-annealing quantity is equal to a difference between the fifth quantity and the optimal reverse primer self-annealing quantity. Calculate a specificity of the primer pair formed by the forward primer and the reverse primer and multiplying by a time to obtain a specificity value; and the eighth objective is equal to a sum of the forward primer self-annealing quantity, the reverse primer self-annealing quantity and the specificity value.

The present invention also provides a PCR method. The PCR method includes mixing the obtained primer pair with a sample DNA, a reaction buffer, a deoxyribonucleic acid mixed solution and a DNA polymerase to prepare a reaction mixed solution, and amplifying the sample DNA in the reaction mixed solution to a predetermined value by the DNA polymerase. Thus, the reaction mixed solution can be used in the PCR method.

BRIEF DESCRIPTION OF THE DRAWINGS

The present invention will become more fully understood from the detailed description given hereinafter and the accompanying drawings which are given by way of illustration only, and thus are not limitative of the present invention, and wherein:

The sole FIGURE is a flow diagram of a method according to a preferred embodiment.

DETAILED DESCRIPTION OF THE INVENTION

With reference to the sole FIGURE, a preferred embodiment of the method for designing the multi-objective primer pair is shown, including an inputting step S1 and a calculating step S2.

The inputting step S1 is used for inputting a DNA template fragment, a length of a forward primer, a length of a reverse primer, at least two objectives and an optimal value for each of the objectives to a computer system. The forward primer and the reverse primer are used for defining a replication starting point of the DNA template fragment, and the at least two objectives are taken as the restricted condition for the primer pair formed by the forward primer and the reverse primer. In the embodiment, the at least two objectives can include two of the first objective, the second objective, the third objective, the fourth objective, the fifth objective, the sixth objective, the seventh objective and the eighth objective.

The calculating step S2 includes generating, by the computer system, a plurality of primer pairs according to the DNA template fragment, the length of the forward primer and the length of the reverse primer. Each primer pair including the forward primer and the reverse primer. The DNA sequence of the forward primer is corresponding to a part of DNA sequence of the DNA template fragment. The DNA sequence of the reverse primer is identical to a part of DNA sequence of the DNA template fragment. The computer system calculates numerical values of the at least two objectives of each of the plurality of primer pairs and inputting the numerical values of the at least two objectives of each of the plurality of primer pairs to a Pareto Chart tool to obtain at least one primer pair, and taking the primer pair as an optimal solution of the DNA template fragment. The principle of the Pareto Chart tool lies in that in a Pareto set, numerical values of total numbers of objectives of a feasible solution exist, dominating the numerical values of corresponding objectives of other feasible solutions, so that the feasible solution is a unique optimal solution. Further, when there is a plurality of optimal solutions, that is, the numerical values of at least two objectives of at least two feasible solutions dominate each other (i.e. do not govern each other) and the numerical values of at least two objectives of at least two feasible solutions dominate the numerical values of corresponding objectives of other feasible solutions, the at least two feasible solutions are the optimal solutions.

In detail, when there is a single optimal solution, that is, the numerical values of the plurality of objectives of one primer pair dominate the numerical values of corresponding objectives of other feasible solutions, the primer pair is the unique optimal solution for the DNA template fragment. Further, when there is a plurality of optimal solutions, that is, the numerical values of at least two objectives of at least two primer pairs dominate each other (i.e. do not govern each other) and the numerical values of at least two objectives of at least two primer pairs dominate the numerical values of corresponding objectives of other primer pairs, the at least two primer pairs are two optimal solutions for the DNA template fragment.

More specifically, the calculating step S2 calculates the numerical value of the first objective $f_1$ by following formula (01). The formula (01) can be shown as follows:

$$f_1 = Tm(\text{fprimer}) = |Tm_{SAN}(\text{fprimer}) - Opt_{Tm}(\text{fprimer})| \quad (01)$$

In formula (01), $Tm_{SAN}$ (fprimer) is used for representing the melting temperature of the forward primer; $Opt_{Tm}$(fprimer) is used for representing the optimal melting temperature of the forward primer; and Tm(fprimer) is used for representing the difference between the melting temperature of the forward primer and the optimal melting temperature of the forward primer.

More specifically, the calculating step S2 calculates the numerical value of the second objective $f_2$ by following formula (02). The formula (02) can be shown as follows:

$$f_2 = Tm(\text{rprimer}) = |Tm_{SAN}(\text{rprimer}) - Opt_{Tm}(\text{rprimer})| \quad (02)$$

In formula (02), $Tm_{SAN}$(rprimer) is used for representing the melting temperature of the reverse primer; $Opt_{Tm}$(rprimer) is used for representing the optimal melting temperature of the reverse primer; and Tm(rprimer) is used for representing the difference between the melting temperature of the reverse primer and the optimal melting temperature of the reverse primer.

The calculating step S2 calculates the numerical value of the third objective $f_3$ by following formulas (03) to (05). The formulas (03) to (05) can be shown as follows:

$$f_3 = Tm_{diff}(\cdot) = \begin{cases} 0, & \text{if } diff_{TM}(\cdot) \le Opt_{Tm\_diff} \\ diff_{Tm}(\cdot) - Opt_{Tm\_diff}, & \text{others} \end{cases} \quad (03)$$

$$diff_{Tm}(\cdot) = |Tm_{SAN}(\text{fprimer}) - Tm_{SAN}(\text{rprimer})| \quad (04)$$

$$Opt_{Tm\_diff} = |Opt_{Tm}(\text{fprimer}) - Opt_{Tm}(\text{rprimer})| \quad (05)$$

In the above formulas, $diff_{Tm}(\cdot)$ is used for representing the temperature difference between the melting temperatures of the forward primer and the reverse primer; $Opt_{Tm\_diff}$ is used for representing the temperature difference between the optimal melting temperature of the forward primer and the optimal melting temperature of the reverse primer; and $Tm_{diff}(\cdot)$ is used for deciding the numerical value of the third objective according to comparison of sizes of the numerical values of $diff_{Tm}(\cdot)$ and $Opt_{Tm\_diff}$.

The calculating step S2 calculates the numerical value of the fourth objective $f_4$ by following formulas (06) to (10). The formulas (06) to (10) can be shown as follows:

$$f_4 = GCclamp_{len_{diff}}(\cdot) = GCclamp(\cdot) + len_{diff}(\cdot) \quad (06)$$

$$GCclamp(\cdot) = \quad (07)$$
$$\begin{cases} 0, & \text{if } (\text{fprimer}_{3'} \text{ end is 'G' or 'C'}) \& (\text{rprimer}_{3'} \text{ end is 'G' or 'C'}) \\ 1, & \text{if } (\text{fprimer}_{3'} \text{ end is 'G' or 'C'}) \| (\text{rprimer}_{3'} \text{ end is 'G' or 'C'}) \\ 2, & \text{if } (\text{neither fprimer}_{3'} \text{ end nor rprimer}_{3'} \text{ end is 'G' or 'C'}) \end{cases}$$

$$len_{diff}(\cdot) = \begin{cases} 0, & \text{if } diff_{len}(\cdot) \le Opt_{len\_diff} \\ diff_{len}(\cdot) - Opt_{len\_diff}, & \text{others} \end{cases} \quad (08)$$

$$diff_{len}(\cdot) = |\text{length}(\text{fprimer}) - \text{length}(\text{rprimer})| \quad (09)$$

$$Opt_{len\_diff} = |Opt_{len}(\text{fprimer}) - Opt_{len}(\text{rprimer})| \quad (10)$$

In the above formulas, $\text{fprimer}_{3'}$ is used for representing the nucleotide type in the 3' end of the forward primer; G, C is used for representing the nucleotide type; $\text{rprimer}_{3'}$ is used for representing the nucleotide type in the 3' end of the reverse primer; length(fprimer) is used for representing the length of the forward primer; length (rprimer) is used for representing the length of the reverse primer; $diff_{len}(\cdot)$ is used for representing the length difference between the forward primer and the reverse primer; $Opt_{len}$ (fprimer) is used for representing the optimal length of the forward primer; $Opt_{len}$ (rPrimer) is used for representing the optimal length of the reverse primer; $Opt_{len\_diff}$ is used for representing the length difference between the optimal length of the forward primer and optimal length of the revere primer; and $Tm_{diff}(\cdot)$ is used for deciding the numerical value of $diff_{Tm}(\cdot)$ according to comparison of sizes of the numerical values of $diff_{Tm}(\cdot)$ and $Opt_{Tm\_diff}$.

The calculating step S2 calculates the numerical values of the fifth and sixth objectives $f_5$ and $f_6$ by following formulas (11) to (13). The formulas (11) to (13) can be shown as follows:

$$f_5 = GC_{proportion}(\text{fprimer}) \quad (11)$$
$$= |GC\%(\text{fprimer}) - Opt_{GC\%}(\text{fprimer})|$$

$$f_6 = GC_{proportion}(\text{rprimer}) \quad (12)$$
$$= |GC\%(\text{rprimer}) - Opt_{GC\%}(\text{rprimer})|$$

$$GC\%(p) = \frac{G_{number}(p) + C_{number}(p)}{|p|}, \quad (13)$$
$$p = \text{fprimer or rprimer}$$

In the above formulas, GC % (fprimer) is used for representing the GC proportion contained in the forward primer; GC % (rprimer) is used for representing the GC proportion contained in the reverse primer; $Opt_{GC\%}$ (fprimer) is used for representing the optimal GC proportion of the forward primer; and $Opt_{GC\%}\%$ (rprimer) is used for representing the optimal GC proportion of the reverse primer.

The calculating step S2 calculates the numerical value of the seventh objective $f_7$ by following formulas (14) to (16). The formulas (14) to (16) can be shown as follows:

$$f_7 = Dimer(\cdot) \quad (14)$$
$$= SelfDimer(\text{fprimer}) + SelfDimer(\text{rprimer}) + CrossDimer(\cdot)$$

$$SelfDimer(p) = \begin{cases} 0, & \text{if } DimerCheck(p,p) \le Opt_{SelfDimer} \\ DimerCheck(p,p) - Opt_{SelfDimer}, & \text{others} \\ p = \text{fprimer or rprimer} \end{cases} \quad (15)$$

$$CorssDimer(p_1, p_2) = \begin{cases} 0, & \text{if } DimerCheck(p_1,p_2) \le Opt_{CrossDimer} \\ DimerCheck(p_1,p_2) - Opt_{CrossDimer}, & \text{others} \\ p_1 = \text{fprimer}, p_2 = \text{rprimer} \end{cases} \quad (16)$$

In the above formulas, DimerCheck(p,p) is used for representing the quantity of bindings generated by the nucleotides of two forward primers; $Opt_{SelfDimer}$ is used for presenting the optimal forward primer self-binding quantity corresponding to the forward primers or the optimal reverse primer self-binding quantity corresponding to the reverse primers; DimerCheck($p_1$, $p_2$) is used for representing the quantity of bindings generated by the nucleotides of the forward and reverse primers; and $Opt_{CrossDimer}$ is used for representing the optimal cross binding quantity of the forward and reverse primers.

The calculating step S2 calculates the numerical value of the eighth objective $f_8$ by following formulas (17) to (18). The formulas (17) to (18) can be shown as follows:

$$f_8 = Specificity_{hairpin} \quad (17)$$
$$= 50 \times specificity(fprimer, rprimer) +$$
$$hairpin(fprimer) + hairpin(rprimer)$$

$$hairpin(p) = \begin{cases} 0, & \text{if } HairpinCheck(p) \leq Opt_{hairpin} \\ HairpinCheck(p) - Opt_{hairpin}, & \text{others} \\ p = fprimer \text{ or } rprimer \end{cases} \quad (18)$$

In the above formulas, specificity(fprimer,rprimer) is used for representing the specificity of the forward primer and the reverse primer; HairpinCheck(p) is used for representing the quantity of self-bindings generated by the nucleotides of the forward primer or the reverse primer; and $Opt_{hairpin}$ is used for representing the optimal forward primer self-binding quantity of the forward primer or the optimal reverse primer self-binding quantity corresponding to the reverse primer.

After calculating the numerical values of the at least two objectives of each of the plurality of primer pairs, the calculating step S2 obtains the at least one optimal solution through a prime pair that a difference between the numerical value of the objective obtained through the Pareto Chart tool and the corresponding optimal value is small, as the at least one primer pair of the at least one optimal solution to be applied to the PCR method, thereby further amplifying a specific DNA fragment with a specific sequence.

For example, when there are three primer pairs, the two objectives of each of the primer pairs are the first and second objectives, and the numerical values of the first and second objectives of the three primer pairs are separately (1.15, 0.1), (2.17, 0.97) and (4.75, 4.94) in sequence. As the numerical values of the first and second objectives of the first primer pair dominate those of the first and second objectives of the second and third primer pairs, the first primer pair is the unique optimal solution for the DNA template fragment.

On the other hand, when the plurality of primer pairs further has the fourth primer pair, and the numerical values of the first and second objectives of the fourth primer pairs is (1.87, 0.78), as the numerical values of the first and second objectives of the first primer pair dominate each other and the numerical values of the first and second objectives of the fourth primer pair dominate those of the first and second objectives of the second and third primer pairs, the first and fourth primer pairs are two optimal solution for the DNA template fragment.

For example, the method for designing the multi-objective primer pair according to the present invention and the conventional single-objective design method select the numerical values calculated by the objectives, separately, and differences between the numerical values and corresponding optimal values can be shown as in table 1 below.

It can be known that the difference between the numerical result of the objectives selected by the method for designing the multi-objective primer pair according to the present invention and the corresponding optimal values is smaller than that obtained by the conventional single-objective design method, so that the method according to the present invention has a better primer pair design efficiency.

TABLE 1

Differences between the numerical values obtained by the present invention and the conventional single-objective design method and the optimal values

| Objective | Present invention | Conventional methods |
|---|---|---|
| First objective | 0.89. | 1.65. |
| Second objective | 0.79. | 1.44. |
| Third objective | 1.23. | 2.2. |
| Fourth objective | 1.11. | 1.56. |
| Fifth objective | 0.89. | 1.65. |
| Sixth objective | 0.79. | 1.44. |
| Seventh objective | Self-dimer (forward primer): 2.61<br>Self-dimer (reverse primer): 2.62<br>Cross-dimer: 3.25 | Self-dimer (forward primer): 3.06<br>Self-dimer (reverse primer): 3.07<br>Cross-dimer: 3.60 |
| Eighth objective | Hairpin (forward primer): 2.26<br>Hairpin (reverse primer): 2.25 | Hairpin (forward primer): 2.55<br>Hairpin (reverse primer): 2.55 |

The invention provides a polymerase chain reaction (PCR) method. The polymerase chain reaction (PCR) method generally refers to using the DNA polymerase with the primer pair matched with the specific sequence of the specific DNA fragment to be amplified to further amplify the specific DNA fragment with the specific sequence by means of thermal cycles containing different temperatures for many times. The polymerase chain reaction (PCR) method includes, but not limited to, restriction fragment length polymorphism (RFLP), nested PCR, real-time PCR, touch-down PCR and hot start PCR, etc. Therefore, the method can amplify the specific DNA fragment with the specific sequence specifically, so that the method can be further applied to DNA cloning, mutation detection or mutagenesis. In addition, the PCR method can be further applied to sequence decoding, gene identification and genetic relationship identification of species, diagnosis of diseases, food detection (such as raw material identification, allergic raw material analysis, etc.) and the like, which shall be understood by a person having ordinary skill in the art.

Generally speaking, the PCR method can include a preparation step mixing the sample DNA, the reaction buffer, mixture of deoxynucleoside triphosphate (mixture of dNTPs), the primer pair and the DNA polymerase to prepare a reaction mixture, wherein the sample DNA includes the specific DNA fragment to be amplified; and an amplification step amplifying the sample DNA in the reaction mixture by the DNA polymerase.

For example, the sample DNA can be from a to-be-tested sample. For instance, the to-be-tested sample can be a tissue from a suspected patient if disease diagnosis is to be performed or the to-be-tested sample can be to-be-tested food if food detection is to be performed. The to-be-tested sample can be subjected to pre-treatment to remove impurities that may affect the amplification step in the to-be-tested sample. For example, when the to-be-tested sample is a whole blood sample, the whole blood sample mixed with an anticoagulant can be centrifugalized for 10 minutes at a rotating speed of 1100 to 1300 g. Thus, a supernatant liquid that is obtained can be taken as the to-be-tested sample.

The reaction buffer is used for providing an environment for the DNA polymerase to amplify the specific DNA fragment and can include either a Tris buffer or other salts such as magnesium chloride ($MgCl_2$), potassium chloride (KCl). The composition of the reaction buffer is different as a result of different types of DNA polymerases are used. Furthermore, mixture of dNTPs can either include at least deoxyadenosine triphosphate (dATP), deoxythymidine triphosphate (dTTP), deoxycytidine triphosphate (dCTP) and deoxyguanosine triphosphate (dGTP), or include isotope-labeled dNTPs. The person having ordinary skill in the art shall be able to understand and further illustration is omitted.

The sample DNA amplification step includes: a denaturing substep denaturing the sample DNA in the reaction mixture to two single-stranded DNA at a high temperature which is higher than 90° C. (such as 94 to 98° C.), with the two single-stranded DNA including a forward single-stranded DNA and a reverse single-stranded DNA; an annealing substep annealing the forward primer to the reverse single-stranded DNA, annealing the reverse primer to the forward single-stranded DNA and replicating the sample DNA from the forward primer and the reverse primer by the DNA polymerase; and a repeating substep repeating the flow till the sample DNA is amplified to a predetermined value.

The denaturing substep includes breaking the hydrogen bonds between the two single-stranded DNA at a high temperature which is higher than 90° C. (such as 94 to 98° C.) to separate the forward single-stranded DNA from the reverse single-stranded DNA; the annealing substep includes forming hydrogen bonds between the forward primer and the reverse single-stranded DNA and between the reverse primer and the forward single-stranded DNA and replicating the sample DNA from the forward primer and the reverse primer by means of the DNA polymerase at a temperature slightly lower than the melting temperatures of the forward primer and the reverse primer (for example, a temperature that is 3 to 5° C. lower); and the repeating substep includes repeating the denaturing substep and the annealing substep (for about 20 to 40 times) to amplify the sample DNA to the predetermined value.

In conclusion, the method for designing the multi-objective primer pair according to the present invention may permit a user to set the optimal value for the selected objective and take the prime pair that a difference between the numerical value of the objective and the corresponding optimal value is small as an optimal solution. Thus, the method for designing the multi-objective primer pair according to the present invention can avoid a large difference between the numerical value of the selected objective and the optimal value, improving the primer pair design efficiency and lowering the time and consumable costs of the PCR experiment.

Although the invention has been described in detail with reference to its presently preferable embodiments, it will be understood by one of ordinary skill in the art that various modifications can be made without departing from the spirit and the scope of the invention, as set forth in the appended claims.

What is claimed is:

1. A method for designing a multi-objective primer pair, comprising:
inputting a DNA template fragment, a length of a forward primer, a length of a reverse primer, at least two objectives and optimal values of each of the at least two objectives to a computer system;
generating, by the computer system, a plurality of primer pairs according to the DNA template fragment, the length of the forward primer and the length of the reverse primer; and
calculating, by the computer system, numerical values of the at least two objectives of each of the plurality of primer pairs and inputting the numerical values of the at least two objectives of each of the plurality of primer pairs to a Pareto Chart tool to determine at least one primer pair to be at least one optimal solution of the DNA template fragment;
wherein, in a circumstance that the at least one optimal solution is a single primer pair, each of the numerical values of the at least two objectives of the single primer pair of the at least one optimal solution dominates a respective one of the numerical values of the at least two objectives of the each of the others of the plurality of primer pairs;
wherein, in a circumstance that the at least one optimal solution is multiple primer pairs, the numerical values of the at least two objectives of each of the multiple primer pairs of the at least one optimal solution dominate each other, and each of the numerical values of the at least two objectives of multiple primer pairs of the at least one optimal solution dominates a respective one of the numerical values of the at least two objectives of each of the others of the plurality of primer pairs;
wherein, the at least two objectives include at least two of a first objective, a second objective, a third objective, a fourth objective, a fifth objective, a sixth objective, a seventh objective and an eighth objective, and one of the at least two objectives is the eighth objective;
wherein, the first objective is defined by a relationship between a melting temperature of a forward primer and a set optimal melting temperature of the forward primer;
wherein, the second objective is defined by a relationship between a melting temperature of a reverse primer and a set optimal melting temperature of the reverse primer;
wherein, the third objective is defined by a relationship among the melting temperature of the forward primer, the melting temperature of the reverse primer, the set optimal melting temperature of the forward primer and the set optimal melting temperature of the reverse primer;
wherein, the fourth objective is defined by a relationship on nucleotide types in 3' ends of both the forward primer and the reverse primer;
wherein, the fifth objective is defined by a relationship between a proportion of 'G' and 'C' type nucleotides in the forward primer and a set optimal GC proportion of the forward primer;
wherein, the sixth objective is defined by a relationship between a proportion of 'G' and 'C' type nucleotides in the reverse primer and a set optimal GC proportion of the reverse primer;
wherein, under a circumstance that a plurality of forward primers and a plurality of reverse primers are provided and a polymerase chain reaction is carried out, the seventh objective is defined by a relationship among a quantity of bindings generated by the nucleotides of two forward primers of the plurality of forward primers, a quantity of bindings generated by the nucleotides of two reverse primers of the plurality of reverse primers, and a quantity of bindings generated by the nucleotides of one of the plurality of forward primers and one of the plurality of reverse primers; and wherein, under the circumstance that the plurality of forward primers and the plurality of reverse primers are provided, and the polymerase chain reaction is carried out, the eighth objective is defined by:

calculating a quantity of self-annealings generated by the nucleotides of one forward primer of the plurality of forward primers to obtain a fourth quantity, wherein if the fourth quantity is not greater than a set optimal forward primer self-annealing quantity, a forward primer self-annealing quantity is equal to 0; if the fourth quantity is greater than the set optimal forward primer self-annealing quantity, the forward primer self-annealing quantity is equal to a difference between the fourth quantity and the set optimal forward primer self-annealing quantity;

calculating a quantity of self-annealings generated by the nucleotides of one reverse primer of the plurality of reverse primers to obtain a fifth quantity, wherein if the fifth quantity is not greater than a set optimal reverse primer self-annealing quantity, a reverse primer self-annealing quantity is equal to 0; if the fifth quantity is greater than the set optimal reverse primer self-annealing quantity, the reverse primer self-annealing quantity is equal to a difference between the fifth quantity and the set optimal reverse primer self-annealing quantity;

calculating a specificity of a primer pair formed by the forward primer and the reverse primer and multiplying by a set factor to obtain a specificity value; and making the eighth objective equal to a sum of the forward primer self-annealing quantity, the reverse primer self-annealing quantity and the specificity value.

2. The method for designing the multi-objective primer pair as claimed in claim 1, wherein the at least two objectives include the first objective calculating a difference between the melting temperature of the forward primer and the set optimal melting temperature of the forward primer and taking an absolute value thereof.

3. The method for designing the multi-objective primer pair as claimed in claim 1, wherein the at least two objectives include the second objective calculating a difference between the melting temperature of the reverse primer and the set optimal melting temperature of the reverse primer and taking an absolute value thereof.

4. The method for designing the multi-objective primer pair as claimed in claim 1, wherein the at least two objectives include the third objective calculating a difference between the melting temperature of the forward primer and the melting temperature of the reverse primer and taking an absolute value thereof to obtain a first difference value, calculating a difference between the optimal melting temperature of the forward primer and the optimal melting temperature of the optimal reverse primer and taking an absolute value thereof to obtain a second difference value, wherein if the first difference value is not greater than the second difference value, the third objective is equal to 0, and if the first difference value is greater than the second difference value, the third objective is equal to a difference between the first difference value and the second difference value.

5. The method for designing the multi-objective primer pair as claimed in claim 1, wherein the at least two objectives include the fourth objective confirming whether nucleotide types in 3' ends of both the forward primer and the reverse primer are 'G' or 'C', and if yes, a GC clamp of the primer pair formed by the forward primer and the reverse primer is equal to 0;

confirming whether nucleotide types in the 3' ends of either the forward primer or the reverse primer are 'G' or 'C', and if yes, the CG clamp is equal to 1;

confirming whether nucleotide types in the 3' ends of the forward primer and the reverse primer are neither 'G' nor 'C', and if yes, the GC clamp is equal to 2;

calculating a length difference between the forward primer and 10 the reverse primer and taking an absolute value thereof to obtain a first length;

setting an optimal length of the forward primer and an optimal length of the reverse primer and calculating a difference between the optimal length of the forward primer and the optimal length of the reverse primer and taking an absolute value thereof to obtain a second length, wherein if the first length is not greater than the second length, a length difference is equal to 0, and if the first length is greater than the second length, the length difference is equal to a difference between the first length and the second length, and the fourth objective is equal to a sum of the GC clamp and the length difference.

6. The method for designing the multi-objective primer pair as claimed in claim 1, wherein the at least two objectives include the fifth objective calculating a difference between the proportion of 'G' and 'C' type nucleotides in the forward primer and the set optimal GC proportion of the forward primer and taking an absolute value thereof.

7. The method for designing the multi-objective primer pair as claimed in claim 1, wherein the at least two objectives include the sixth objective calculating the proportion of 'G' and 'C' type nucleotides in the reverse primer and the set optimal GC proportion of the reverse primer and taking an absolute value thereof.

8. The method for designing the multi-objective primer pair as claimed in claim 1, wherein the at least two objectives include the seventh objective calculating the quantity of bindings generated by the nucleotides of two forward primers of the plurality of forward primers and a plurality of reverse primers provided simultaneously when a polymerase chain reaction is carried out to obtain a first quantity, wherein if the first quantity is not greater than an optimal forward primer self-binding quantity, a forward primer self-binding quantity is equal to 0;

if the first quantity is greater than the optimal forward primer self-binding quantity, the forward primer self-binding quantity is equal to a difference between the first quantity and the optimal forward primer self-binding quantity; and calculating the quantity of bindings generated by the nucleotides of two reverse primers to obtain a second quantity, wherein if the second quantity is greater than an optimal reverse primer self-binding quantity, the reverse primer self-binding quantity is equal to a difference between the second quantity and the optimal reverse primer self-binding quantity, and calculating the quantity of bindings generated by the nucleotides of one of the plurality of forward primers and one of the plurality of reverse primers to obtain a third quantity, wherein if the third quantity is not greater than an optimal cross-binding quantity, a primer cross-binding quantity is equal to 0;

if the third quantity is greater than the optimal cross-binding quantity, the primer cross-binding quantity is equal to a difference between the third quantity and the optimal cross-binding quantity, and the seventh objective is equal to a sum of the forward primer self-binding quantity, the reverse primer self-binding quantity and the primer cross-binding quantity.

* * * * *